United States Patent [19]

Middleton et al.

[11] Patent Number: 4,568,478

[45] Date of Patent: Feb. 4, 1986

[54] FLUOROXY COMPOUND SOLUTIONS

[75] Inventors: William J. Middleton, Chadds Ford, Pa.; Shlomo Rozen, Ramat Aviv, Israel

[73] Assignee: E. I. Dupont de Nemours and Company, Wilmington, Del.

[21] Appl. No.: 601,589

[22] Filed: Apr. 18, 1984

[51] Int. Cl.$^4$ ............ A62D 3/00; C01B 7/00; C07C 69/62

[52] U.S. Cl. .......... 252/187.2; 260/453 R X; 560/227; 568/435; 568/420; 568/319; 568/354; 568/397; 568/484; 568/807

[58] Field of Search ............ 260/453 R X; 252/187.2

[56] References Cited

U.S. PATENT DOCUMENTS 3,415,865 12/1968 Prager et al. ............ 260/453 R X
3,420,866 1/1969 Prager et al. ............ 260/453 R X
3,684,786 8/1972 Chandrasekaran ......... 260/453 R X

OTHER PUBLICATIONS

Porter et al., *J. Am. Chem. Soc.*, 79:5625–5627 (1957).
Cady et al., *J. Am. Chem. Soc.*, 75:2501–2502 (1953).
Menefee et al., *J. Am. Chem. Soc.*, 76:2020–2021 (1954).
Thompson et al., *J. Am. Chem. Soc.*, 89:2263–2267 (1967).
Barton et al., *Chem. Comm.*, 122–123 (1972).
Rozen et al., *Tetrahedron Letters No. 8*, 725–727 (1979).
Rozen et al., *J. Am. Chem. Soc.*, 101:2782–2784 (1979).
Rozen et al., *J. Fluorine Chem.*, 16:19–31 (1980).
Rozen et al., *J. Org. Chem.*, 45:672–678 (1980).
Lerman et al., *J. Org. Chem.*, 46:4629–4631 (1981); 48:724–727 (1983).

*Primary Examiner*—Henry R. Jiles
*Assistant Examiner*—Robert C. Whittenbaugh

[57] ABSTRACT

There is disclosed a solution of at least one fluoroxy compound, wherein said solution has a fluoroxy compound concentration of at least 0.5 meq/liter; said concentration containing about 35 to 100% of an acyl hypofluorite, based on the total number of equivalents of fluoroxy compounds present. The acyl hypofluorite has the formula $X(CF_2)_n COOF$ wherein X is H or F and n is 5 to 16. The solution is prepared by treating a suspension of a corresponding specified alkali salt with excess $F_2$, and is useful as a selective fluorinating agent.

14 Claims, No Drawings

FLUOROXY COMPOUND SOLUTIONS

BACKGROUND OF THE INVENTION

This invention relates to solutions of fluoroxy compounds and, in particular, to such solutions wherein one of the fluoroxy compounds is an acyl hypofluorite.

Acyl hypofluorites of less than five carbon atoms have previously been reported. Cady et al., *J. Am. Chem. Soc.*, 75, 2501 (1953), disclose the preparation of trifluoroacetyl hypofluorite ($CF_3CO_2F$) in low yield by fluorination of trifluoroacetic acid. Menefee et al., *J. Am. Chem. Soc.*, 76, 2020 to 2021 (1954), disclose the preparation of pentafluoropropionyl hypofluorite, $C_2F_5CO_2F$, and heptafluorobutyryl hypofluorite by reaction of fluorine with the corresponding acids. The authors report that by placing about 2 ml of water in the reaction vessel and removing a trap, the yield of explosive product was greatly increased.

Thompson et al., *J. Am. Chem. Soc.*, 89, 2263 to 2267 (1967), disclose the preparation of 1,1-bis(fluoroxy)perfluoropropane and 2,2-bis(fluoroxy)perfluoropropane by direct fluorination of the monosodium salt of perfluoroacetone hydrate, $(CF_3)_2C(OH)ONa$. The authors state that, in contrast, direct fluorination of perfluoroacetone hydrate yields $(CF_3)_2CFOF$ and that, in regard to the fluorination of trifluoroacetic acid and its salts, the acid affords rather low yields of the hypofluorite, $CF_3C(O)OF$ whereas the salts give yields of up to 60% $CF_3CF(OF)_2$.

U.S. Pat. No. 3,415,865 ('865 patent), issued to Prager et al. on Dec. 10, 1968, discloses perfluoroalkyl polyfluoroxy compounds having the formula $R_f(OF)_n$ wherein $R_f$ is a perfluorinated alkyl radical having from 1 to 18 carbon atoms and n is an integer from 2 to 12. The disclosed compounds are stated to be useful fluorinated oxidizing agents and are prepared by direct fluorination of compounds having a molecular structure in which at least one oxygen atom is directly linked to a carbon atom. Salts of carboxylic acids are included among the starting materials and may give mixtures of mono-oxyfluoro- and dioxyfluoro-substituted compounds. Alkali metal salts are disclosed as suitable. The use of an inert gaseous diluent, such as $N_2$, for fluorine is also disclosed and examples of fluorination of the sodium salts of perfluorohexanoic and perfluorodecanoic acids are given.

U.S. Pat. No. 3,420,866, issued to Prager et al. on Jan. 7, 1969, discloses the same compounds and process as the '865 patent. U.S. Pat. No. 3,442,927, issued to Thompson et al. on May 6, 1969, discloses fluoroxy compounds having the formula $(R)_nC(F)_mOF$ wherein R is a perfluorinated alkyl radical having 1 to 18 carbon atoms, n is an integer from 1 to 3, and m equals 3n.

Barton et al., *Chem. Comm.* 122 to 123 (1972), discuss the behavior of several different types of fluoroxy compounds as electrophilic fluorinating agents, and state that there is some suggestion that tertiary fluoroxy compounds might be disposed to free radical reactions.

Rozen et al., *Tetrahedron Lett.*, 725 to 728 (1979), report that an oxidative solution results when elemental fluorine is passed into a suspension of $CF_3COONa$ in "freon" at $-75°$ C., and that up to 50% of the oxidizing ability of the solution is due to the presence of $CF_3CF_2OF$, although all of the oxidizing compounds present are presumably of the perfluoroxyfluoride type. The authors disclose the use of this solution to effect electrophilic fluorination.

Rozen et al., *J. Am. Chem. Soc.*, 101, 2782 to 2783 (1979), report on the fluoroxy solution mentioned in the previous paragraph and disclose that use of excess fluorine leads to bis-fluoroxy compounds. The authors state that, if $CF_3COONa$ is not completely dried, the $F^-$ is immediately almost completely hydrated and $CH_3COOF$ is the main reaction product. Use of $CF_3COOF$ as an agent to form fluorohydrins is also disclosed.

Rozen et al., *J. Fluorine Chem.*, 16, 19 to 31 (1980), disclose the use of solutions prepared by reacting $F_2$ with $CF_3COONa$ in absence of $H_2O$ as fluorinating agents to convert enol acetates to the corresponding α-fluoroketones. Rozen et al., *J. Org. Chem.*, 45, 672 to 678 (1980), disclose the reaction of sodium trifluoroacetate with fluorine in the presence of traces of water or HF to give mainly trifluoroacetyl hypofluorite, $CF_3COOF$ and the reaction of this in situ preparation with stilbenes and diphenylacetylene.

Lerman et al., *J. Org. Chem.*, 46, 4629 to 4631 (1981), disclose the use of $CH_3COOF$ as an electrophilic fluorination agent for activated aromatic rings. Lerman et al., *J. Org. Chem.*, 48, 724 to 727 (1983), disclose the use of $CH_3COOF$ as a fluorinating agent for 1,3-dicarbonyl derivatives.

SUMMARY OF THE INVENTION

The present invention provides a solution of at least one fluoroxy compound, said solution having a fluoroxy compound concentration of at least 0.5 meq/liter; said concentration containing, based on the total number of equivalents of fluoroxy compounds present, about 35 to 100% of an acyl hypofluorite fluoroxy compound of the formula $X(CF_2)_nCOOF$; said solution prepared by contacting a suspension of a salt of the formula $X(CF_2)_nCOOM$ in a liquid, inert fluorocarbon medium with excess $F_2$, wherein X is H or F, n is 5 to 16 and M is Li, Na, K or Cs, provided that the other fluoroxy compounds in said solution are also reaction products resulting from contacting of said suspension with $F_2$. The invention also provides use of said solutions to prepare certain fluorinated compounds.

DETAILED DESCRIPTION OF THE INVENTION

The concentration of fluoroxy compounds present in the solutions according to the present invention is at least 0.5 meq/liter. Solutions having a fluoroxy compound concentration of at least 0.5 to about 60 meg/liter are preferred, at least 0.5 to about 50 meq/liter is most preferred. Solutions having a fluoroxy compound concentration of more than about 60 meq/liter are difficult and time-consuming to prepare. Moreover, the possibility of explosive decomposition becomes significant above 60 meq/liter, and protective safeguards such as barricades and/or special reactors capable of withstanding explosion become necessary. The concentration of fluoroxy compounds present in the solution (meq/liter), can be determined by the titration procedure described in Example 1.

The fluoroxy compound concentration of the solutions according to the present invention contains about 35 to 100% acyl hypofluorite, based on the total number of equivalents of fluoroxy compounds present. Preferably, the fluoroxy compound concentration contains about 70 to 100% acyl hypofluorite, because these solutions provide greater selectivity and higher yields of products in fluorination reactions.

The solutions of the present invention are stable during long term storage at 0° C. In contrast to $CF_3CO_2F$ or $C_2F_5CO_2F$ which decompose rapidly at 0° C., the present solutions remain active as selective fluorinating agents after being stored for several weeks to several months at 0° C. in containers constructed of inert materials such as Pyrex ® glass, or selected synthetic polymers such as polytetrafluoroethylene. The solutions of the present invention can be used as reagents in aqueous reaction mixtures without appreciable loss of activity due to hydrolysis. Moreover, since the acyl hypofluorites of the present solutions are nonvolatile and the solutions are stable to storage when cold, the fluoroxy compound concentration in the solutions can easily be measured and the solutions are easily handled.

The acyl hypofluorite present in the solution of the invention has the formula $X(CF_2)_nCOOF$ wherein X is H or F and n is 5 to 16, preferably 6 to 12. The solution is prepared by contacting a suspension of a salt of the formula $X(CF_2)_nCOOM$, wherein X and n are as previously defined and M is Li, Na, K or Cs, with excess elemental fluorine in a liquid, inert fluorocarbon medium. Preferably, M is K because potassium salts are more readily available. In the present invention, it is preferable that the suspension of salt to be contacted with fluorine contain water, preferably about 0.2 to 2 moles of water per mole of anhydrous salt. Most preferably, water is provided by using a hydrated salt prepared by recrystallization from water.

An inert, liquid fluorocarbon medium is used to suspend the salt and to dissolve the final product mixture. Suitable liquids include perfluorinated hydrocarbons, such as perfluorooctanes, perfluorohexanes, perfluorocyclohexane, and the like; perfluorocyclic ethers, such as perfluoro-2-butyltetrahydrofuran; and halofluorocarbons, such as fluorotrichloromethane, 1,1,2-trifluorotrichloroethane, and the like. The medium is empirically selected on the basis of the end-use of the fluoroxy solution.

The fluoroxy solution of the invention is prepared by contacting elemental fluorine with the aforesaid suspension of fluoroxyacid salt, preferably in the presence of water. The fluorine is diluted with nitrogen or other inert gas and is used in a concentration of about 0.5 to 5% by volume based on the total volume of inert gas and fluorine. A concentration of about 1% by volume of fluorine in inert gas is preferred. Preferably, during preparation of the solution, a temperature of about −78° to −20° C., most preferably about −50° to −20° C., is maintained.

Solutions prepared according to the present invention are stable during storage for several months at about −20° to 0° C. without appreciable loss of their activity. The exact composition of the fluoroxy solution of the invention is not known but $^{19}$F-NMR spectroscopic data indicate that it is comprised of a mixture of acyl hypofluorite (1), hypofluorite (2), and bis-hypofluorite (3)

wherein R is $X(CF_2)_n$ and X and n are as previously defined.

The number of equivalents of the acyl hypofluorite (1) contained in the fluoroxy compound concentration of the final product is dependent on the hypofluorite hydration state of the starting salt. Salts having one or more mole equivalent of water of hydration generally give solutions with a fluoroxy compound concentration containing about 35 to 100% acyl hypofluorite, based on the total number of equivalents of fluoroxy compound present. Aqueous-recrystallized, hydrated salts give solutions with a fluoroxy compound concentration containing about 50 to 100% acyl hypofluorite. The number of equivalents of acyl hypofluorite present can be determined by addition of the solution to stilbene and gas chromatographic analysis of the resulting fluoroalkanoyloxy-stilbene adduct.

The fluoroxy solution of the invention is useful as a selective, electrophilic fluorinating agent giving good product yields. Enol acetates of the general formula (4)

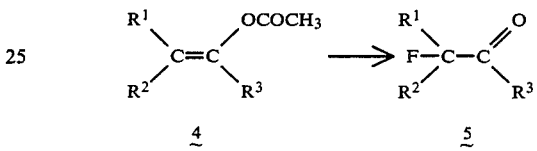

wherein $R^1$, $R^2$ and $R^3$ are individually hydrogen, alkyl, substituted alkyl, aryl, or substituted aryl; or $R^2$ and $R^3$ are part of a cyclic ring system, react with fluoroxy solutions of the invention to give α-fluoroketones (5) in good yields, i.e., about 40 to 80% by weight.

Electron-rich olefins (6) where $R^4$ and $R^5$ are individually defined as for $R^1$, react with the fluoroxy solution of the invention to give adducts (7).

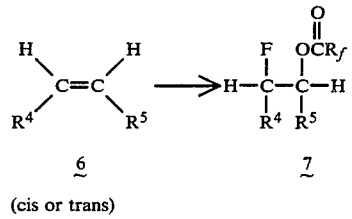

(cis or trans)

The group $R_f$ in the adduct (7) is equivalent to $X(CF_2)_n$ in the starting acyl hypofluorite.

Electrophilic fluorination according to the present invention is effected in an inert liquid fluorocarbon medium previously described for preparation of the fluoroxy solutions. The process is conducted at a temperature of about −78° to +20° C., preferably about −78° to −10° C., to minimize side reactions. Best yields are obtained in the presence of excess fluorinating agent, e.g., about 1.5 meq of total oxidant per mmole of substrate to be fluorinated. Yields are comparable to those obtained with $CF_3OF$ or $CF_3CO_2F$, but the latter reagents are gaseous and are difficult to handle or measure. The present electrophilic fluorination process affords the preparation of fluoroagrichemicals and fluoropharmaceuticals in a controlled, selective manner. Biologically active compounds which can be prepared by the electrophilic fluorination process of the invention include 2,4-dichlorophenoxy fluoroacetic acid, 2,4,5-trichlorophenoxy fluoroacetic acid, 3- fluorodiazepam, triamcinolone, paramethasone, dexamethasone, betamethasone, fluprednisolone, flucytosine, 5-fluorouracil, and 3-fluoro-d-alanine.

The invention is illustrated by the following examples in which all temperatures are in degrees Celsius and all percentages are by weight unless otherwise stated. In the examples the vibrating mixer was equipped with a hollow shaft for liquid or gas delivery and gas chromatographic analysis was conducted with a Supelco Co. 6'×⅛" stainless column packed with 20% FS-1265 on 60/80 Gas Chrome-R. The number of equivalents of acyl hypofluorite contained in the mixed fluoroxy solutions illustrated by Examples 2, 3 and 4, was determined from the equation:

$$\% \text{ acyl hypofluorite } (A) = \frac{\text{No. of equivalents of } A}{\text{Total No. of equivalents of fluoroxy compounds}} \times 100.$$

EXAMPLE 1

Preparation of Electrophilic Fluorinating Agent from Potassium Perfluorooctanoate Hydrated potassium perfluorooctanoate (1.5 mol of $H_2O$/mol of salt, 6.36 g) was suspended in 450 mL of perfluoro-2-butyltetrahydrofuran and the resulting mixture was cooled to $-78°$ under nitrogen. The mixture was agitated with a vibrating mixer while fluorine (1% by volume in nitrogen, approximately 40 mmole) was bubbled into the mixture for 24 hours. A 10 mL aliquot of the resulting solution was treated with excess acidified aqueous potassium iodide and titrated with 0.01M sodium thiosulfate. The titration indicated that the concentration of fluoroxy compounds in the solution was 6.0 meq/liter. The solution was filtered through glass wool and then stored at 0°.

EXAMPLES 2-6

Using a procedure similar to that described in Example 1 other fluoroxy solutions useful as electrophilic fluorinating agents were prepared. The concentration of acyl hypofluorite was measured by adding stilbene to the solution and measuring the amount of fluoro-perfluoroalkanoyloxy stilbene adduct produced.

EXAMPLE 7

Preparation of Electrophilic Fluorinating Agent from Potassium Perfluorooctanoate Hydrate Potassium perfluorooctanoate (6 g) was stored in a desiccator over water for 3 days. After this period, the increased weight of the salt indicated the formation of the 1.0–1.5 hydrate. The hydrated salt was fluorinated in perfluoro-2-butyltetrahydrofuran with 1% fluorine in nitrogen until a solution containing 2.5 to 3 meq/l of fluoroxy compounds was formed.

EXAMPLE 8

Fluorination: Preparation of 1-Fluoro-2-perfluorooctanoyloxystilbene

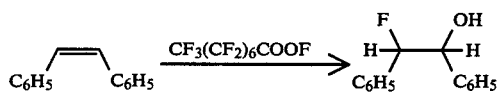

A fluoroxy solution (140 mL) prepared by the procedure described in Example 3 was transferred to a reaction flask previously cooled to $-10°$ and diluted with similarly cooled 1,1,2-trifluorotrichloroethane (140 mL). A 10 mL aliquot of the resulting solution was treated with acidified aqueous potassium iodide and then titrated with 0.01M sodium thiosulfate. The titration indicated that the concentration of fluoroxy compounds remained unchanged before and after transfer and was after dilution at 0.593 mequiv of fluoroxy compounds/150 mL. cis-Stilbene (428 mg, 2.38 mmole) was added to solution flask in one portion in cooled 1,1,2-trifluorotrichloroethane (20 mL) and the resulting mixture was stirred at $-10°$. After 10 min, titration of an aliquot indicated that fluoroxy compounds were no longer present. The resulting reaction mixture was washed with aqueous 10% sodium thiosulfate (200 mL), 10% potassium carbonate (200 mL), and saturated sodium chloride (200 mL) solutions and dried over anhydrous magnesium sulfate. Filtration and removal of solvent under reduced pressure left an oil. Gas chromatographic analysis of the oil indicated a 70% yield of 1-fluoro-2-perfluorooctanoyloxystilbene as a mixture of erythro and threo isomers. A sample prepared similarly

| Example | Salt | Medium | Fluoroxy Compound Concentration (meq/l) | % Acyl hypofluorite |
| --- | --- | --- | --- | --- |
| 2 | potassium perfluorooctanoate (recrystallized from $H_2O$, 60 g) | perfluoro-2-butyltetrahydrofuran (450 mL)(at $-20°$ C.) | 34.1 | 79 |
| 3 | potassium perfluorooctanoate (recrystallized from $H_2O$, 8.69 g) | perfluoro-2-butyltetrahydrofuran (450 mL) | 4.5 | 79 |
| 4 | potassium perfluorooctanoate (recrystallized from $H_2O$, 10.2 g) | 1,1,2-trifluorotrichloroethane (450 mL, $-25°$ C.) | 7.6 | 77 |
| 5 | potassium perfluorooctanoate (1.0 mol of $H_2O$/mol of salt, 8.15 g) | perfluoro-2-butyltetrahydrofuran (450 mL) | 3.3 | |
| 6 | potassium perfluorooctanoate (recrystallized from $H_2O$, 31.52 g) | perfluoro-2-butyltetrahydrofuran (450 mL) | 41.9 | | was converted to the 1-fluoro-2-hydroxystilbene by treatment of the crude oil (1.3 g) with anhydrous potassium carbonate (250 mg) in methanol (5 mL). After 30 min, the resulting reaction mixture was diluted with ether (100 mL), washed with aqueous 1N oxalic acid solution until acidic, washed with water (50 mL) and saturated sodium chloride solution (50 mL), and dried over anhydrous MgSO$_4$. Filtration, removal of solvent under reduced pressure, and purification by flash column chromatography (silica, methylene chloride-hexane 1:1) yielded a chromatographically faster-moving isomer of 1-fluoro-2-hydroxystilbene (90 mg) and a slower-moving isomer of 1-fluoro-2-hydroxystilbene (40 mg) both as white crystalline solids. Faster moving isomer: $^1$H NMR (90 MHz, CDCl$_3$) δ 4.97 (dm, J=12 Hz, 1H, CHOH), 5.50 (dd, J=40, 5.3 Hz, 1H, CHF), 7.27 (m, 10H, aromatic); $^{19}$F NMR (94.1 MHz, CDCl$_3$) −184.43 (dd, J=45, 12.5 Hz); slower moving isomer: $^1$H NMR (90 MHz, CDCl$_3$) δ 4.90 (dd, J=12, 6.7 Hz, 1H, CHOH), 5.40 (dd, 41.3, 6.7 Hz, 1H, CHF), 7.20 (m, 10H, aromatic); $^{19}$F NMR (94.1 MHz, CDCl$_3$) −181.27 (dd, 47, 12.5 Hz).

The invention being claimed is:

1. A solution of at least one fluoroxy compound, said solution containing an acyl hypofluorite compound of the formula RCOOF and having a fluoroxy compound concentration of at least 0.5 meq/liter; said concentration containing, based on the total number of equivalents of fluoroxy compounds present, about 35 to 100% of RCOOF; other fluoroxy compounds in said solution having the formulae RCF$_2$OF and RCF(OF)$_2$; said solution prepared by contacting a suspension of a salt of the formula RCOOM in a liquid, inert fluorocarbon medium with excess F$_2$, wherein for each occurrence R is X(CF$_2$)$_n$-, n is 5 to 16, X is H or F and M is Li, Na, K or Cs.

2. A solution according to claim 1 wherein the fluoroxy compound concentration is at least 0.5 to about 60 meq/liter.

3. A solution according to claim 2 wherein the concentration is at least 0.5 to about 50 meq/liter.

4. A solution according to claim 1 wherein the fluoroxy compound concentration contains about 70 to 100% acyl hypofluorite.

5. A solution according to claim 1 wherein the suspension contains water.

6. A solution according to claim 5 wherein about 0.2 to 2 moles of water per mole of anhydrous salt is present.

7. A solution according to claim 6 wherein the salt is a hydrated salt prepared by recrystallization from water.

8. A solution according to claim 1 wherein the F$_2$ is diluted with N$_2$ or other inert gas and is used in a concentration of about 0.5 to 5% by volume based on the total volume of inert gas and fluorine.

9. A solution according to claim 8 wherein the F$_2$ is diluted with inert gas and is used in a concentration of about 1%.

10. A solution according to claim 1 wherein the temperature during preparation thereof is about −78° to −20° C.

11. A solution according to claim 10 wherein the temperature is about 50° to −20° C.

12. A solution according to claim 1 wherein n is 6 to 12.

13. A solution according to claim 1 wherein M is K and the medium is perfluoro-2-butyltetrahydrofuran or 1,1,2-trifluorotrichloroethane.

14. A solution according to claim 7 wherein the fluoroxy compound concentration contains about 70 to 100% acyl hypofluorite; the F$_2$ is diluted with N$_2$ or other inert gas and is used in a concentration of about 1% by volume, based on the total volume of inert gas and fluorine; the temperature during preparation thereof is about 50° to −20° C.; n is 6 to 12; M is K; and the medium is perfluoro-2-butyltetrahydrofuran or 1,1,2-trifluorotrichloroethane.

* * * * *